United States Patent [19]
Tsuchida et al.

[11] Patent Number: 5,962,278
[45] Date of Patent: Oct. 5, 1999

[54] CELLULOSE-PRODUCING BACTERIA

[75] Inventors: Takayasu Tsuchida; Naoto Tonouchi; Akira Seto; Yukiko Kojima; Masanobu Matsuoka; Fumihiro Yoshinaga, all of Kawasaki, Japan

[73] Assignee: Bio-Polymer Research Co., Ltd., Kawasaki, Japan

[21] Appl. No.: 08/973,757

[22] PCT Filed: Feb. 24, 1997

[86] PCT No.: PCT/JP97/00514

§ 371 Date: Feb. 3, 1998

§ 102(e) Date: Feb. 3, 1998

[87] PCT Pub. No.: WO97/40135

PCT Pub. Date: Oct. 30, 1997

[30] Foreign Application Priority Data

Apr. 23, 1996 [JP] Japan ................................. 8/123951
May 22, 1996 [JP] Japan ................................. 8/149763
Jun. 14, 1996 [JP] Japan ................................. 8/174393

[51] Int. Cl.$^6$ ............................. C12N 1/20; C12P 19/04
[52] U.S. Cl. ..................... 435/101; 435/252.1; 435/823
[58] Field of Search ................................ 435/101, 252.1, 435/823

[56] References Cited

U.S. PATENT DOCUMENTS 5,580,782 12/1996 Beppu et al. ........................ 435/252.1

OTHER PUBLICATIONS

ACS Computer Abstract CA112–177044(19) Brown WO8912107, Dec. 14, 1989.
ACS Computer Abstract CA124–230187(17) Naoki et al. JP0803494, Feb. 6, 1996.
ACS Computer Abstract CA123–309914(23) Krystynowicz Alina et al "Biosynthesis of bacterial cellulose and its application", 1995.
ACS Computer Abstract CA122–050889(05) Schmauder et al "Formation and application of bacterial cellulose in research, industry and medicine", 1994.

*Primary Examiner*—Herbert J. Lilling
*Attorney, Agent, or Firm*—Oblon, Spivak, McClelland, Maier & Neustadt, P.C.

[57] ABSTRACT

This invention relates to a microorganism that is capable of producing a cellulosic product (referred to hereinafter as a "cellulose-producing bacterium") and belongs to a novel subspecies which is substantialy negative or very slightly positive in oxidation of acetates and lactates. This invention also relates to novel saccharide analog-resistant strains, amino acid analog-resistant strains and levan sucrase-defective strains.

Further, this invention relates to a method for the production of cellulosic material (bacterial cellulose: "BC"), which comprises culturing these novel bactria and to bacterial cellulose which may be thus obtained.

A larger amount of bacterial cellulose may be produced by culturing *Acetobacter xylinum* subsp. *nonacetoxidans*, the present resistant strains and the levan sucrase-defective strains, which have been derived and bred from the cellulose-producing bacteria, than by culturing the BPR 2001 strain in the medium containing especially sucrose or glucose as carbon sources.

8 Claims, No Drawings

CELLULOSE-PRODUCING BACTERIA

TECHNICAL FIELD

This invention relates to a microorganism that is capable of producing a cellulosic product (referred to hereinafter as a "cellulose-producing bacterium") and belongs to a novel subspecies which is substantialy negative or very slightly positive in oxidation of acetates and lactates. This invention also relates to novel saccharide analog-resistant strains, amino acid analog-resistant strains and levan sucrase-defective strains.

Further, this invention relates to a method for the production of cellulosic material (bacterial cellulose: "BC"), which comprises culturing these novel bactria and to bacterial cellulose which may be thus obtained.

BACKGROUND ART

Since BC is edible as well as tasteless and odorless, it is utilized in the food industry. BC's high dispensability in water further provides it with a lot of industrial applications, such as to maintain moisture and viscosity of food, cosmetics or coating agents, to strengthen food materials, to improve stability of food, and to be used as low-calorie additives and an emulsion stabilizer.

BC is characterized by a sectional width of its fibrils which is smaller by two orders of magnitude than that of other kinds of cellulose such as those derived from wood pulp.

Owing to such structural and physical feature of microfibril, a homogenized BC has plenty of industrial applications as a strengthening agent for polymers, especially hydrophilic polymers. Products prepared by solidification of the macerated BC in the form of a lump or paper show a high elastic modulus in tension owing to the above feature, and are therefore expected to have excellent mechanical properties for use in various kinds of industrial materials.

The strains conventionally used in the production of BC include Acetobacter strains such as *Acetobacter xylinum* subsp. *sucrofermentans* such as the BPR 2001 strain, *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, *Acetobacter xylinum* ATCC10821; and strains derived and bred from those strains by means of various kinds of mutagenesis treatment and recombination of genes; and strains derived and generated from those strains by using known mutagens such as NTG (nitrosoguanidine).

The taxonomic characters of BPR 2001 strain are as follows:

Morphology: rod, Gram stain: negative, Spore formability: negative, Behavior toward oxygen: aerobic, Catalase: positive, Oxidase: negative, Formation of acetic acid from ethanol: positive, Oxidation of acetates: positive, Oxidation of lactates: positive.

The PQQ non-generating strain obtained from the BPR 2001 strain has been also used. One example of the above PQQ non-generating strain, designated the BPR 3001c was deposited at the National Institute of Bioscience and Human-Technology, Agency of Industrial Science and Technology (1-3, Higashi 1-chome, Tsukuba-shi, Ibaraki-ken 305 Japan) on May 2, 1994 under accession number FERM P-14297, and then transferred on May 12, 1995 to the deposit under the terms of the Budapest Treaty on the International Recognition of the Deposit of Microorganisms for the Purposes of Patent Procedure and Regulation under accession number FERM BP-5100.

Mutants include a levan sucrase-defective mutant in which the production of levan is suppressed.

Other mutants include the sulfur agent-resistant strain designated BPR 3001D, pyrimidine analogue-resistant strain designated BPR 3001I and DHO-DHase inhibitors-resistant strain designated BPR3001N, which were also deposited at the National Institute of Bioscience and Human-Technology, Agency of Industrial Science and Technology on May 25, 1994 under accession number FERM P-14330, on Jun. 10, 1994 under accession number FERM P-14362, and on Jun. 10, 1994 under accession number FERM P-14361, respectively. Further, there have been disclosed the cellulose-producing bacteria transformed with a gene for an enzyme involved in sucrose metabolism (WO95/32279) and the cellulose-producing bacteria transformed with an extracellular invertase gene and its secretion-accelerating gene (Japanese Patent Application Hei 7 (1995)-252021).

BPR 2001 was deposited at the National Institute of Bioscience and Human-Technology, Agency of Industrial Science and Technology (1-3, Higashi 1-chome, Tsukuba-shi, Ibaraki-ken 305 Japan) on Feb. 24, 1993 under accession number FERM P-13466, and then transferred on Feb. 7, 1994 to the deposit under the terms of the Budapest Treaty on the International Recognition of the Deposit of Microorganisms for the Purposes of Patent Procedure and Regulation under accession number FERM BP-4545.

The present inventors have carried out many kinds of researches in order to provide novel cellulose-producig bacteria for the production of a large amount of BC using sucrose or glucose as sugar source, in an efficient manner, and have found a novel subspieces which is substantialy negative or very slightly positive in oxidation of acetates and lactates.

The cellulose-producing bacteria grow and produce BC, while incorporating and metabolizing carbon sources such as saccharides, and biosynthesizing amino acids or incorporating and metabolizing them form a culture medium. The present inventors have therefore carried out many kinds of researches, taking into consideration the increase of capability of incorporation and metabolism of saccharides and amino acids, so that strains which are improved in the cellulose production may be obtained. As a result, the present inventors have surprisingly found that the additon of some compounds (saccharides analogs or amino acid analogs) could prevent the growth of the bacteria. The present inventors have obtained strains with an improved productivity of BC by selecting the resistant strains against these analogs, and completed the present invention.

Levan sucrase (EC2.4.1.10) is known to decompose and metabolize sucrose. This enzyme has two activities, (1) hydrolysis activity of sucrose into glucose and fructose, and (2) transfructosylation activity to produce glucose and levan from sucrose. The latter activity is not preferred in terms of BC production since it will produce levan as a by-product. It will be very advantageous in the production and purification of BC, if the accumulation of levan is suppressed. The present inventors have already disclosed in the Japanese Patent Application Hei 7 (1995)-252021 that by deriving the levan sucrase-defective strain and incorporating the gene of an extracellular invertase or a levan sucrase with a reduced levan productibity into said strain, the accumulation of levan will be reduced and the cellulose may be efficiently produced.

DISCLOSURE OF INVENTION

This invention relates to *Acetobacter xylinum* subsp. *nonacetoxidans*, which are substantialy deficient (negative) or very slightly positive in oxidation of acetates and lactates.

The present *Acetobacter xylinum* subsp. *nonacetoxidans* include strains designated as S-35'-3, 757-3-5-11 and 184-2-2, which have been deposited at the National Institute of Bioscience and Human-Technology, Agency of Industrial Science and Technology (1-3, Higashi 1-chome, Tsukuba-shi, Ibaraki-ken 305 Japan) on Apr. 12, 1996 under accession number FERM P-15563, FERM P-15564, and FERM P-15565, respectively, and then transferred on Feb. 10, 1997 to the deposit under the terms of the Budapest Treaty on the International Recognition of the Deposit of Microorganisms for the Purposes of Patent Procedure and Regulation under accession number FERM BP-5814, FERM BP-5815, and FERM BP-5816, respectively.

This invention also relates to novel saccharide analog-resistant strains, amino acid analog-resistant strains of the cellulose-producing bacteria.

The "saccharide analog" is defined in the present specification to mean the compound that is analogous to the material used for carbon sources such as glucose, and the addition of which will prevent or suppress the growth of the bacteria or the cellulose production because of competition with the saccharides.

Thus, the saccharide analog includes 2-deoxy-D-glucose (DG), 6-deoxy-glucosamine, 1-thio-D-glucose, 5-thio-D-glucose, 1-methyl-glucose and phlorizin.

The "amino acid analog" is defined in the present specification to mean the compound that is analogous to amino acids, and the addition of which will prevent or suppress the growth of the bacteria or the cellulose production because of competition with the amino acids.

Thus, the amino acid analog includes analog compounds to the amino acids such as phenylalanine, serine and methionine, for example, p-fluoro phenylananine, o-methylserine and ethionine.

The present novel resistant strains may be generated from the above-mentioned various strains such as the present *Acetobacter xylinum* subsp. *nonacetoxidans* by using known mutagens such as NTG (nitrosoguanidine).

The novel levan sucrase-defective strain, LD-2 was derived and bred from the above 757-3-5-11 strain by using the similar mutagenesis method. This strain has been deposited under the terms of the Budapest Treaty on the International Recognition of the Deposit of Microorganisms for the Purposes of Patent Procedure and Regulation at the National Institute of Bioscience and Human-Technology, Agency of Industrial Science and Technology (1–3, Higashi 1-chome, Tsukuba-shi, Ibaraki-ken 305 Japan) on Jan. 22, 1997 under accession number FERM BP-5789.

Further, this invention relates to a method for the production of cellulosic material, which comprises culturing the present *Acetobacter xylinum* subsp. *nonacetoxidans*, the various resistant strains and defective strains, and to bacterial cellulose which may be thus obtained.

The present *Acetobacter xylinum* subsp. *nonacetoxidans* has been produced by isolating Acetobacters with a high productivity of cellulose from natural sources such as flowers and fruits, screening desired strains and identifying their bacterial properties. It has been found form the comparison of the bacterial properties among the strains shown in the following Table 1 that the present *Acetobacter xylinum* subsp. *nonacetoxidans* is different from IFO15237 strain or *Acetobacter xylinum* subsp. *sucrofermentans* such as the BPR 2001 strain, but is a novel subspecies which is substantialy deficient (negative) or very slightly positive in oxidation of acetates and lactates.

TABLE 1

Bacterial Properties

| Properties | 184-2-2 | S-35'-3 | 757-3-5-11 | BPR2001 | IFO15237 |
|---|---|---|---|---|---|
| Morphology | rod | rod | rod | rod | rod |
| Gram strain | − | − | − | − | − |
| Spore | | | | | |
| Formability | − | − | − | − | − |
| Mobility | − | − | − | − | − |
| Behavior toward Oxygen | aerobic | aerobic | aerobic | aerobic | aerobic |
| Oxidase | − | − | − | − | − |
| Catalase | + | + | + | + | + |
| Oxidation or Fermentation | 0 | 0 | NG | 0 | 0 |
| Formation of acetic acid from ethanol | + | + | + | + | + |
| Oxidation of acetates | very slight | very slight | − | + | + |
| Oxidation of lactates | very slight | very slight | − | + | + |
| Quinone type | Q-10 | Q-10 | Q-10 | Q-10 | Q-10 |
| GC contents (mol %) | 63 | 62 | 62 | 61 | 62 |
| Formation of cellulosic material | + | + | + | + | + |
| Formation of aqueous brown pigments in GYC medium | − | − | NG | − | − |
| Formation of γ-pyron from D-glucose | − | − | − | − | − |
| Formation of γ-pyron from D-fructose | − | − | − | − | − |
| Formation of 5-ketogluconic acid from D-glucose | + | + | − | − | + |
| Formation of 2,5-diketo-gluconic acid from D-glucose | − | − | − | − | − |
| Ketogenesis from glycerol | + | + | + | + | + |
| Ability to utilize amino acids for growth in the presence of D-mannitol | | | | | |
| L-glutamine | + | + | + | + | − |
| L-asparagine | + | + | + | + | − |
| Glycine | very slight | very slight | + | − | − |
| L-threonine | − | − | − | − | − |
| L-tryptophan | + | + | + | + | − |

NG: not grown in the test medium

Carbon sources in the culture media useful in the present production method may include sucrose, glucose, fructose, mannitol, sorbitol, galactose, maltose, erythritol, glycerol, ethyleneglycol, ethanol and the like. In addition, sucrose may be combined with dextrin hydrolysate, citrus molasses, beet molasses, squeezed juice from beet or sugar cane, juice from citrus and the like.

Nitrogen sources useful in the present production method include organic or inorganic ones such as ammonium salts comprising ammonium sulfate, ammonium chloride, ammonium phosphate; nitrates; and urea. Nitrogen-containing natural nutrients may be also used including Bact-Peptone, Bact-soytone, Yeast-Extract and Bean-Condensate. A trace amount of organic nutrients may be further added including, 2,7,9-tricarboxy-1H pyrrolo [2,3,5]-quinoline-4,5-dione.

When the mutants with nutritional requirement for amino acids is used, for examples, such required nutrients should be supplemented in the culture media. Inorganic nutrients include phosphate salts, magnesium salts, calcium salts, iron salts, manganese salts, cobalt salts, molybdate salts, hematite salts, chelete metal salts and the like.

Methods for the production of cellulose by culturing cellulose-producing bacteria such as those belonging to the genus Acetobacter have been known in prior arts such as, for example, Japanese Patent Laid-Open Application Sho 62(1987)-265990, Japanese Patent Laid-Open Application Sho 63(1988)-202394 and Japanese Patent Publication Hei 6(1994)-43443. As a nutrient medium suitable for the culture of the cellulose-producing bacteria, Schramm/Hestrin medium is known, which contains carbon source, peptone, yeast extract, sodium phosphate and citric acid (Schramm et al., J. General Biology, 11, pp.123–129, 1954).

Other culture media are also known, which further contain corn steep liquor (CSL), malt extract and the like.

The nutrients known up to now as an accelerator for the cellulose production include inositol, fitinic acid and pyrroloquinoline quinone (PQQ) (Japanese Patent Publication Hei 5(1993)-1718; Mitsuo TAKAI, Japan TAPRI Journal, Vol. 42, No. 3, pp. 237–244).

The present inventors have also found that production of the cellulosic product is increased by addition of carboxylic acids or their salts (Japanese Patent Laid-Open Application Hei 7 (1995)-39386), invertase (Japanese Patent Laid-Open Application Hei 7 (1995)-184677), methionine (Japanese Patent Laid-Open Application Hei 7 (1995)-184675), a saponin (Japanese Patent Application Hei 6(1994)-214334).

The pH range for the culture according to the present invention is controlled between 3 and 7, preferably around 5. The culturing temperature is kept in a range between 10 and 40° C., preferably between 25 and 35° C. Oxygen supply into a culture tank may contain from 1 to 100% oxygen, desirably 21 to 80%. The contents of these components in the culture media and amounts of the bacteria to be inoculated into the media may be optionally determined by those skilled in the art depending on the culture method to be used.

The culture according to the present invention may be carried out by any culture conditions such as static, shaking, and aerobic agitated conditions. It is one of advantages of the present invention that the cellulose productivity will not be affected even under shaking culture, or aerobic agitated conditions. The present invention may adopt any culture operation method such as batch fermentation, fed batch fermentation, repeated batch fermentation and continuous fermentation. These culture conditions and operation methods may be optionally modified.

Means for agitation may be optionally selected from any known means such as impellers, air-lift fermentors, pump-driven recirculation of the fermentor broth and any combination of these means.

The cellulosic product produced according to the present method may be collected as such, or subjected to a treatment for removing materials other than the cellulosic product, such as bacterial cells and the like.

Such impurities may be removed from the cellulosic products by, for example, washing with water, diluted acids or alkalis, dehydration under pressure; treatment with a bleach such as sodium hypochlorite and hydrogen peroxide, a lytic enzyme such as lysozyme; treatment with a surfactant such as sodium laurylsulfate and deoxycholic acid; washing with heating at from a room temperature to 200° C.; or combinations thereof.

The cellulosic products thus obtained according to the present invention means cellulose, those comprising hetero polysaccharides which contains cellulose as a main chain, or those comprising glucans such as $\beta$-1, $\beta$-3, $\beta$-1,2 and the like. The other components than cellulose in the hetero polysaccharides are six-carbon saccharides such as mannose, fructose, galactose, xylose, arabinose, rhamnose, and gluconic acid, five-carbon saccharides, organic acids and the like.

The polysaccharides may be homogeneous materials or consist of two or more polysaccharides via hydrogen bonds.

Best Mode for Carrying Out the Invention

The present invention will be further illustrated with reference to the following examples.

EXAMPLE 1

Generation of *Acetobacter xlyinum* subsp. *nonacetoxidans*

It is generally known that Acetobacter strains are present in flowers and fruits (Bergey's Manual of Systematic Bacteriology (1984) Vol. 1, p. 268). The present starins were isolated from these materials. At first, the starting material was diluted with a stelirized liquid medium mainly consisting of Schramm/Hestrin medium (Biochemical Journal, 58 (1954), pp.345–352): Glucose 20 g/l, Yeast extract 5 g/l, Peptone 5 g/l, Na$_2$HPO$_4$ 2.7 g/l, Citric acid. H$_2$O 1.2 g/l, Ethanol 2 ml/l, Acetic acid 5 ml/l, Cycloheximide (fungicide) 100 mg/l, pH 5.0. The resluting mixture was inoculated into the same liquid medium and incubated in an accumulated culture, followed by a static culture for seven days at 28° C. The culture broth containing pericles formed was diluted, inoculated onto an agar flat plate containing the above medium plus 20 g/l of agar and incubated for seven days at 28° C., followed by isolation of colonies of the cellulose-producing bacteria. The desired stains were screened from these colonies, and their bacterial properties were identified by a standard method well known in the art. The results are shown in Table 1.

EXAMPLE 2

Production of Bacterial Cellulose by the Culture of *Acetobacter xylinum* subsp. *nonacetoxidans*

(1) Jar culture

Main media: CSL (4%)—Sucrose (4%) or CSL (4%)—Glucose (4%)

Strains: 184-2-2, 757-3-5-11, BPR2001

Culture method:

A Roux flask (750 ml volume) containing 100 ml of the above main medium was inoculated with a lyophilized stock solution of the above strains (1 ml). The cultures were grown for three days at 28° C. under non-shaking conditions. After the completion of the static culture, the Roux flask was vigorously shaken and the contents were aseptically filtered through gauze to separate cellulose strips from the cell bodies. A spiral baffle flask (300 ml volume) containing 67.5 ml of the above main medium was inoculated with the resulting cell mixture (7.5 ml) and subjected to a seed-culture with a shaking apparatus for three days at 28° C. under the agitation at 180 rpm and shaking width of 2 cm.

After the completion of the culture, the flask contents were transferred into a sterilized blender and disrupted for 3 min at 10,000 rpm. The disrupted contents were used in the following main culutre as a seed cell mixture.

The seed cell mixture (60 ml) was aseptically inoculated into a small jar fermenter (total volume of 1,000 ml) containing 540 ml of a sterilized main medium and subjected to the main culture at 30° C. maintaining pH 5.0 by means of 1 N NaOH or 1 N $H_2SO_4$ and keeping the dissolved oxygen (DO) concentration in the range of 3.0–21.0% by automatically controlling a rotating speed of impellers (the initial rotating speed of 400 rpm). The accumulated amounts of BC were shown in Table 2 and Table 3.

TABLE 2

BC accumulation under the culture with sucrose after 45 hr

| Strains | Amount of accumulated BC (g/l) |
| --- | --- |
| 184-2-2 | 10.0 |
| 757-3-5-11 | 9.0 |
| BPR2001 (control) | 5.5 |

TABLE 3

BC accumulation under the culture with glucose after 45 hr

| Strains | Amount of accumulated BC (g/l) |
| --- | --- |
| 184-2-2 | 7.0 |
| 757-3-5-11 | 7.9 |
| BPR2001 (control) | 1.8 |

(2) Static culture

Main media: CSL (2%)—Sucrose (4%)

Strains: S-35'-3, BPR2001

Culture method:

A Roux flask (250 ml volume) containing 50 ml of the above main medium was inoculated with a lyophilized stock solution of the above strains (0.5 ml). The cultures were grown for three days at 28° C. under non-shaking conditions. After the completion of the static culture, the resulting culture mixture was then subjected to the following main culture.

The resulting culture mixture (5 ml) was inoculated into a Roux flask (250 ml volume) containing 45 ml of the above main medium. The culturing area of the flask was 75 cm$^2$ and its depth was 0.67 cm. The static culture was carried out for three days at 28° C. to give the BC accumulation as shown in Table 4 below.

TABLE 4

| Strains | Amount of accumulated BC (g/l) |
| --- | --- |
| S-35'-3 | 10.0 |
| BPR2001 (control) | 1.3 |

TABLE 5

CSL-Suc(or Glc) medium

| Component | Final conc. (mM) |
| --- | --- |
| $(NH_4)_2SO_4$ | 25 |
| $KH_2PO_4$ | 7.3 |
| $MgSO_4.7H_2O$ | 1.0 |
| $FeSO_4.7H_2O$ | 0.013 |
| $CaCl_2.2H_2O$ | 0.10 |
| $Na_2MoO_4.2H_2O$ | 0.001 |
| $ZnSO_4.7H_2O$ | 0.006 |
| $MnSO_4.5H_2O$ | 0.006 |
| $CuSO_4.5H_2O$ | 0.0002 |
| Vitamin Mixture (see below) | 10 ml/l |
| Carbon Source | as specified |
| CSL | as specified |
| Anti-foam agent | 0.01 v/v % |
| Final pH | 5.0 ± 0.2 |

(Sucrose or glucose: 40 g/l; CSL: 40 or 20 ml/l, if not specified otherwise)

TABLE 6

Vitamin Mixture

| component | mg/L |
| --- | --- |
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzonic Acid | 20 |
| Folic Acid | 0.2 |
| Biotin | 0.2 |

EXAMPLE 3

Generation of Saccharide-Resistant Strains

Confirmation of the resistance against 2-deoxy-D-glucose (DG)

The 757-3-5-11 strain was inoculated on a plate containing the minimum medium shown in Table 10 with various concentration values of DG. After seven-day culture at 28° C., the number of the colonies formed on each plate was observed.

TABLE 7

The number of the colonies of 757-3-5-1 observed on the plate containing DG

| DG (mmol/L) | Number of the colonies |
| --- | --- |
| 0 | 88 |
| 100 | 26 |
| 150 | 1 |
| 200 | 0 |
| 250 | 0 |

Mutagenesis treatment of 757-3-5-11

The strains were grown in CSL (2%)—Fru medium (Table 11) for three hours at 28° C. This pre-culture was collected, washed with 10 mM phospate buffer (pH 6.0) and subjected to the mutagenesis treatment in 10 mM phospate buffer containing 40 mg/ml of NTG for 30 min at 30° C. The treated cells were collected, washed as above and cultured in CSL (2%)—Fru medium at 28° C. overnight to fix the mutation. As a result, the mutants were obtained with a survival rate of about 1%.

Selection of the saccharide analog (DG)-resistant strains

The above-treated 757-3-5-11 strains (about 4,000 colonies) were inoculated on a plate containing 200 mmol/L of DG (about 170 colonies per plate). They were cultured for seven days at 28° C. and 109 strains were selected from the formed colonies.

EXAMPLE 4

The above 109 strains were cultured according to the following method and the amount of BC accumulation was determined.

At first, a Roux flask (250 ml volume) containing 50 ml of CSL (2%)—Fru medium was inoculated with the above strains and incubated for three days at 28° C. under non-shaking conditions.

(1) Flask culture

The Roux flask was vigorously shaken to release the cells from the resulting cellulose film and 7.5 ml of this culture mixture was inoculated into a conical flask with baffles (300 ml volume) containing 68 ml of CSL (2%)—Glc (2%) medium, followed by a main culture for three days at 28° C. ubder agitation at 150 rpm.

As a result, six DG-resistant strains showed superior BC productivity to their parent strain, 757-3-5-11, as seen in Table 8.

One of the above six strains, d-40-3 has been deposited at the National Institute of Bioscience and Human-Technology, Agency of Industrial Science and Technology (1-3, Higashi 1-chome, Tsukuba-shi, Ibaraki-ken 305 Japan) on Apr. 25, 1996 under accession number FERM P-15603, and then transferred on Feb. 10, 1997 to the deposit under the terms of the Budapest Treaty on the International Recognition of the Deposit of Microorganisms for the Purposes of Patent Procedure and Regulation under accession number FERM BP-5817.

TABLE 8

Increase of BC productivity of DG-resistant strains in a flask culture

| Strains | BC (g/L) |
| --- | --- |
| 757-3-5-11 (parent strain) | 4.1 |
| d-13 | 4.4 |
| d-15 | 4.3 |
| d-40-3 | 5.6 |
| d-63 | 4.6 |
| d-83 | 4.6 |
| d-89 | 5.2 |

(2) Jar culture

Strains: DG-resistant strain (d-40-3), 757-3-5-11

Culture method:

A Roux flask (750 ml volume) containing 100 ml of CSL (2%)—Glc (2%) medium was inoculated with a lyophilized stock solution of each strain (1 ml). The cultures were grown for three days at 28° C. under non-shaking conditions. After the completion of the static culture, the Roux flask was vigorously shaken and the contents were aseptically filtered through gauze to separate cellulose strips from the cell bodies. A spiral baffle flask (300 ml volume) containing 67.5 ml of the above medium was inoculated with the resulting cell mixture (7.5 ml) and subjected to a seed-culture with a shaking apparatus for three days at 28° C. under the agitation at 180 rpm and shaking width of 2 cm.

After the completion of the culture, the flask contents were transferred into a sterilized blender and disrupted for 3 min at 10,000 rpm. The disrupted contents were used in the following main culutre as a seed cell mixture.

The seed cell mixture (60 ml) was aseptically inoculated into a small jar fermenter (total volume of 1,000 ml) containing 540 ml of a sterilized CSL (4%)—Glc (4%) medium (Table 11) and subjected to the main culture at 30° C. maintaining pH 5.0 by means of ammonia gas or 1 N $H_2SO_4$ and keeping the dissolved oxygen (DO) concentration in the range of 3.0–21.0% by automatically controlling a rotating speed of impellers (the initial rotating speed of 400 rpm). The accumulated amounts of BC were shown in Table 9.

TABLE 9

Increase of BC productivity of DG-resistant strain in a jar culture

| Strains | BC (g/L) |
| --- | --- |
| 757-3-5-11 (parent strain) | 9.3 |
| d-40-3 | 10.5 |

TABLE 10

Minimum medium

| | |
| --- | --- |
| $K_2HPO_4$ | 0.01 (%) |
| $KH_2PO_4$ | 0.5 |
| $MgSO_4.7H_2O$ | 0.025 |
| KCl | 0.01 |
| $CaCl_2.2H_2O$ | 0.01 |
| $FeCl_3.6H_2O$ | 0.005 |
| Na glutamate.$H_2O$ | 0.4 |
| Glucose | 1.0 |
| pH | 5.0 |

TABLE 11

CSL-Fru (or Glc) medium

| Component | (%) |
| --- | --- |
| Fructose or Glucose | 2.0 or 4.0 |
| $KH_2PO_4$ | 0.1 |
| $MgSO_4.7H_2O$ | 0.025 |
| $(NH_4)_2SO_4$ | 0.33 |
| Vitamin Mixture | 1.0 |
| Salt Mixute | 1.0 |
| CSL | 2.0 or 4.0 |
| pH | 5.0 |

TABLE 12

Salt mixture

| | |
| --- | --- |
| $FeSO_4.7H_2O$ | 360 (mg/L) |
| $CaCl_2.2H_2O$ | 1470 |
| $Na_2MoO_2.2H_2O$ | 242 |
| $ZnSO_4.7H_2O$ | 173 |
| $MnSO_4.5H_2O$ | 139 |
| $CuSO_4.5H_2O$ | 5 |

TABLE 13

Vitamin mixture

| component | (mg/L) |
| --- | --- |
| Inositol | 200 |
| Niacin | 40 |
| Pyridoxine HCl | 40 |

TABLE 13-continued

Vitamin mixture

| component | (mg/L) |
|---|---|
| Thiamine HCl | 40 |
| Ca Pantothenate | 20 |
| Riboflavin | 20 |
| p-Aminobenzonic Acid | 20 |
| Folic Acid | 0.2 |
| Biotin | 0.2 |

EXAMPLE 5

Generation of p-fluoro-phenylalanine (PFP) Resistant Strains

Confirmation of the resistance against PFP

The 184-2-2 strain was inoculated on a plate containing the minimum medium shown in Table 10 with various concentration values of PFP. After seven-day culture at 28° C., the number of the colonies formed on each plate was observed.

TABLE 14

The number of the colonies of 184-2-2 observed on the plate containing PFP

| PFP (mM) | Number of the colonies |
|---|---|
| 0 | 66 |
| 0.1 | 30 |
| 0.5 | 11 |
| 1 | 0 |
| 4 | 0 |

Mutagenesis treatment of 184-2-2

The strains were grown in CSL (2%)—Suc medium (Table 23) for three hours at 28° C. This pre-culture was collected, washed with 10 mM phospate buffer (pH 6.0) and subjected to the mutagenesis treatment in 10 mM phospate buffer containing 40 mg/ml of NTG for 30 min at 30° C. The treated cells were collected, washed as above and cultured in CSL (2%)—Suc medium at 28° C. overnight to fix the mutation. As a result, the mutants were obtained with a survival rate of about 1%.

Selection of PFP-resistant strains

The above-treated 184-2-2 strains (about 12,000 colonies) were inoculated on a plate containing 1 mM of PFP (about 120 colonies per plate). They were cultured for seven days at 28° C. and 62 strains were selected from the formed colonies.

Production of BC

The above 62 strains were cultured according to the following method and the amount of BC accumulation was determined.

At first, a Roux flask (750 ml volume) containing 100 ml of CSL (2%)—Suc medium (Table 23) was inoculated with the above strains and incubated for three days at 28° C. under non-shaking conditions.

(1) Flask culture

The Roux flask was vigorously shaken to release the cells from the resulting cellulose film and 7.5 ml of this culture mixture was inoculated into a conical flask with baffles (300 ml volume) containing 68 ml of CSL (2%)—Suc medium (Table 23), followed by a main culture for three days at 28° C. ubder agitation at 150 rpm.

As a result, six PFP-resistant strains showed superior BC productivity to their parent strain, 184-2-2, as seen in Table 15.

One of the above six strains, BPR-M6 has been deposited at the National Institute of Bioscience and Human-Technology, Agency of Industrial Science and Technology (1-3, Higashi 1-chome, Tsukuba-shi, Ibaraki-ken 305 Japan) on May 30, 1996 under accession number FERM P-15657, and then transferred on Feb. 10, 1997 to the deposit under the terms of the Budapest Treaty on the International Recognition of the Deposit of Microorganisms for the Purposes of Patent Procedure and Regulation under accession number FERM BP-5820.

TABLE 15

Increase of BC productivity of PFP-resistant strains in a flask culture

| Strains | BC (g/L) |
|---|---|
| 184-2-2 (parent strain) | 3.4 |
| BPR-M4 | 3.7 |
| M6 | 3.7 |
| M49 | 3.8 |
| M50 | 5.0 |
| M51 | 3.6 |
| M58 | 3.8 |

(2) Jar culture

Strains: PFP-resistant strain (BPR-M6), 184-2-2

Culture method:

A Roux flask (750 ml volume) containing 100 ml of CSL (2%)—Suc medium (Table 23) was inoculated with a lyophilized stock solution of each strain (1 ml). The cultures were grown for three days at 28° C. under non-shaking conditions. After the completion of the static culture, the Roux flask was vigorously shaken and the contents were aseptically filtered through gauze to separate cellulose strips from the cell bodies. A spiral baffle flask (300 ml volume) containing 67.5 ml of the above medium was inoculated with the resulting cell mixture (7.5 ml) and subjected to a seed-culture with a shaking apparatus for three days at 28° C. under the agitation at 150 rpm.

After the completion of the culture, the flask contents were transferred into a sterilized blender and disrupted for 3 min at 10,000 rpm. The disrupted contents were used in the following main culutre as a seed cell mixture.

The seed cell mixture (60 ml) was aseptically inoculated into a small jar fermenter (total volume of 1,000 ml) containing 540 ml of a sterilized CSL (2%)—Suc medium (Table 23) and subjected to the main culture at 30° C. maintaining pH 5.0 by means of ammonia gas or 1 N $H_2SO_4$ and keeping the dissolved oxygen (DO) concentration in the range of 3.0–21.0% by automatically controlling a rotating speed of impellers (the initial rotating speed of 400 rpm). The accumulated amounts of BC were shown in Table 16.

TABLE 16

Increase of BC productivity of PFP-resistant strain in a jar culture

| Strains | BC (g/L) (after 38 hours) |
|---|---|
| 184-2-2 (parent strain) | 8.2 |
| BPR-M6 | 10.1 |

EXAMPLE 6

Generation of o-methylserine Resistant Strains

Confirmation of the resistance against o-methylserine

The 184-2-2 strain was inoculated on a plate containing the minimum medium shown in Table 10 with various concentration values of o-methylserine. After seven-day culture at 28° C., the number of the colonies formed on each plate was observed.

TABLE 17

The number of the colonies of 184-2-2 observed on the plate containing o-methylserine

| o-Methylserine (mM) | Number of the colonies |
|---|---|
| 0 | 59 |
| 1 | 52 |
| 5 | 49 |
| 10 | 9 |
| 40 | 0 |

Mutagenesis treatment of 184-2-2

The strains were grown in CSL (2%)—Suc medium (Table 23) for three hours at 28° C. This pre-culture was collected, washed with 10 mM phospate buffer (pH 6.0) and subjected to the mutagenesis treatment in 10 mM phospate buffer containing 40 mg/ml of NTG for 30 min at 30° C. The treated cells were collected, washed as above and cultured in CSL (2%)—Suc medium at 28° C. overnight to fix the mutation. As a result, the mutants were obtained with a survival rate of about 1%.

Selection of o-methylserine-resistant strains

The above-treated 184-2-2 strains (about 12,000 colonies) were inoculated on a plate containing 40 mM of o-methylserine (about 120 colonies per plate). They were cultured for seven days at 28° C. and 60 strains were selected from the formed colonies.

Production of BC

The above 60 strains were cultured according to the following method and the amount of BC accumulation was determined.

At first, a Roux flask (750 ml volume) containing 100 ml of CSL (2%)—Suc medium (Table 23) was inoculated with the above strains and incubated for three days at 28° C. under non-shaking conditions.

(1) Flask culture

The Roux flask was vigorously shaken to release the cells from the resulting cellulose film and 7.5 ml of this culture mixture was inoculated into a conical flask with baffles (300 ml volume) containing 68 ml of CSL (2%)—Suc medium (Table 23), followed by a main culture for three days at 28° C. ubder agitation at 150 rpm.

As a result, seven o-methylserine-resistant strains showed superior BC productivity to their parent strain, 184-2-2, as seen in Table 18.

One of the above seven strains, BPR-N52 has been deposited at the National Institute of Bioscience and Human-Technology, Agency of Industrial Science and Technology (1-3, Higashi 1-chome, Tsukuba-shi, Ibaraki-ken 305 Japan) on May 30, 1996 under accession number FERM P-15655, and then transferred on Feb. 10, 1997 to the deposit under the terms of the Budapest Treaty on the International Recognition of the Deposit of Microorganisms for the Purposes of Patent Procedure and Regulation under accession number FERM BP-5818.

TABLE 18

Increase of BC productivity of o-Methylserine-resistant strains in a flask culture

| Strains | BC (g/L) |
|---|---|
| 184-2-2 (parent strain) | 3.4 |
| BPR-N13 | 5.8 |
| N16 | 6.5 |
| N26 | 5.9 |
| N41 | 5.4 |
| N42 | 4.4 |
| N52 | 6.7 |
| N58 | 4.4 |

(2) Jar culture

Strains: o-Methylserine-resistant strain (BPR-N52), 184-2-2

Culture method:

A Roux flask (750 ml volume) containing 100 ml of CSL (2%)—Suc medium (Table 23) was inoculated with a lyophilized stock solution of each strain (1 ml). The cultures were grown for three days at 28° C. under non-shaking conditions. After the completion of the static culture, the Roux flask was vigorously shaken and the contents were aseptically filtered through gauze to separate cellulose strips from the cell bodies. A spiral baffle flask (300 ml volume) containing 67.5 ml of the above medium was inoculated with the resulting cell mixture (7.5 ml) and subjected to a seed-culture with a shaking apparatus for three days at 28° C. under the agitation at 150 rpm.

After the completion of the culture, the flask contents were transferred into a sterilized blender and disrupted for 3 min at 10,000 rpm. The disrupted contents were used in the following main culutre as a seed cell mixture.

The seed cell mixture (60 ml) was aseptically inoculated into a small jar fermenter (total volume of 1,000 ml) containing 540 ml of a sterilized CSL (2%)—Suc medium (Table 23) and subjected to the main culture at 30° C. maintaining pH 5.0 by means of ammonia gas or 1 N $H_2SO_4$ and keeping the dissolved oxygen (DO) concentration in the range of 3.0–21.0% by automatically controlling a rotating speed of impellers (the initial rotating speed of 400 rpm). The accumulated amounts of BC were shown in Table 19.

TABLE 19

Increase of BC productivity of o-Methylserine resistant strain in a jar culture

| Strains | BC (g/L) (after 38 hours) |
|---|---|
| 184-2-2 (parent strain) | 8.2 |
| BPR-N52 | 10.2 |

EXAMPLE 7

Generation of Ethionine Resistant Strains

Confirmation of the resistance against ethionine

The 757-3-5-11 strain was inoculated on a plate containing the minimum medium shown in Table 10 with various concentration values of ethionine. After seven-day culture at 28° C., the number of the colonies formed on each plate was observed.

TABLE 20

The number of the colonies of 757-3-5-11 observed on the plate containing ethionine

| Ethionine (mM) | Number of the colonies |
|---|---|
| 0 | 41 |
| 0.05 | 24 |
| 0.1 | 6 |
| 0.2 | 0 |
| 0.5 | 0 |

Mutagenesis treatment of 757-3-5-11

The strains were grown in CSL (2%)—Suc medium (Table 23) for three hours at 28° C. This pre-culture was collected, washed with 10 mM phospate buffer (pH 6.0) and subjected to the mutagenesis treatment in 10 mM phospate buffer containing 40 mg/ml of NTG for 30 min at 30° C. The treated cells were collected, washed as above and cultured in CSL (2%)—Suc medium at 28° C. overnight to fix the mutation. As a result, the mutants were obtained with a survival rate of about 1%.

Selction of ethionine-resistant strains

The above-treated 757-3-5-11 strains (about 6,000 colonies) were inoculated on a plate containing 0.2 mM of ethionine (about 60 colonies per plate). They were cultured for seven days at 28° C. and 76 strains were selected from the formed colonies.

Production of BC

The above 76 strains were cultured according to the following method and the amount of BC accumulation was determined.

At first, a Roux flask (750 ml volume) containing 100 ml of CSL (2%)—Suc medium (Table 23) was inoculated with the above strains and incubated for three days at 28° C. under non-shaking conditions.

(1) Flask culture

The Roux flask was vigorously shaken to release the cells from the resulting cellulose film and 7.5 ml of this culture mixture was inoculated into a conical flask with baffles (300 ml volume) containing 68 ml of CSL (2%)—Suc medium (Table 23), followed by a main culture for three days at 28° C. ubder agitation at 150 rpm.

As a result, seven ethionine-resistant strains showed superior BC productivity to their parent strain, 757-3-5-11, as seen in Table 21.

One of the above seven strains, BPR-P35 has been deposited at the National Institute of Bioscience and Human-Technology, Agency of Industrial Science and Technology (1-3, Higashi 1-chome, Tsukuba-shi, Ibaraki-ken 305 Japan) on May 30, 1996 under accession number FERM P-15656, and then transferred on Feb. 10, 1997 to the deposit under the terms of the Budapest Treaty on the International Recognition of the Deposit of Microorganisms for the Purposes of Patent Procedure and Regulation under accession number FERM BP-5819.

TABLE 21

Increase of BC productivity of ethionine-resistant strains in a flask culture

| Strains | BC (g/L) |
|---|---|
| 757-3-5-11 (parent strain) | 5.6 |
| BPR-P12 | 7.2 |
| P25 | 6.2 |
| P27 | 5.7 |
| P28 | 7.1 |
| P30 | 6.4 |
| P35 | 6.3 |
| P38 | 6.8 |

(2) Jar culture

Strains: Ethionine-resistant strain (BPR-P35), 757-3-5-11

Culture method:

A Roux flask (750 ml volume) containing 100 ml of CSL (2%)—Suc medium (Table 23) was inoculated with a lyophilized stock solution of each strain (1 ml). The cultures were grown for three days at 28° C. under non-shaking conditions. After the completion of the static culture, the Roux flask was vigorously shaken and the contents were aseptically filtered through gauze to separate cellulose strips from the cell bodies. A spiral baffle flask (300 ml volume) containing 67.5 ml of the above medium was inoculated with the resulting cell mixture (7.5 ml) and subjected to a seed-culture with a shaking apparatus for three days at 28° C. under the agitation at 150 rpm.

After the completion of the culture, the flask contents were transferred into a sterilized blender and disrupted for 3 min at 10,000 rpm. The disrupted contents were used in the following main culutre as a seed cell mixture.

The seed cell mixture (60 ml) was aseptically inoculated into a small jar fermenter (total volume of 1,000 ml) containing 540 ml of a sterilized CSL (2%)—Suc medium (Table 23) and subjected to the main culture at 30° C. maintaining pH 5.0 by means of ammonia gas or 1 N $H_2SO_4$ and keeping the dissolved oxygen (DO) concentration in the range of 3.0–21.0% by automatically controlling a rotating speed of impellers (the initial rotating speed of 400 rpm). The accumulated amounts of BC were shown in Table 22.

TABLE 22

Increase of BC productivity of ethionine-resistant strain in a jar culture

| | BC (g/L) | |
|---|---|---|
| Strains | (after 24 hours) | (after 42 hours) |
| 757-3-5-11 (parent strain) | 5.0 | 9.0 |
| BPR-P35 | 9.3 | 10.1 |

TABLE 23

CSL-Suc medium

| Component | (%) |
|---|---|
| Sucrose | 4.0 |
| $KH_2PO_4$ | 0.1 |
| $MgSO_4.7H_2O$ | 0.025 |
| $(NH_4)_2SO_4$ | 0.33 |
| Vitamin Mixture | 1.0 (See Table 13) |
| Salt Mixture | 1.0 (See Table 12) |
| CSL | 2.0 |
| pH | 5.0 |

EXAMPLE 8

Generation of Levan Sucrase-Defective Strains

The 757-3-5-11 strain was subjected to the same mutagenesis treatment as above, and inoculated on a plate containing the minimum medium shown in Table 10 using sucrose insteaad of glucose. The small non-mucoidal colonies producing no levan were selected as candidate strains. Further, the two strains (LD-1 and LD-2) produciing cellulose well in the Glc-CSL medium (Table 11) were selected from the above candidates. Table 24 shows the production of cellulose and polysaccharide as by-product by these two strains in CSL-Glc and CSL-Suc media (Table 5). No activity of levan sucrase was observed in these two strains by the usual method (H. Yanase et al., Biosci. Biotech. Biochem., Vol. 55 pp. 1383–1390, 1991), confirming that these two strains are levan sucrase-defective strains.

TABLE 24

Production of cellulose and accumulation of polysaccharide from glucose and sucrose by the levan sucrase-defective strains

|         | Sucrose   |                | Glucose   |                      |
| ------- | --------- | -------------- | --------- | -------------------- |
| Strains | Cellulose | Polysaccharide | Cellulose | Polysaccharide (g/L) |
| LD-1    | 1.4       | 0.6            | 4.2       | 0.9                  |
| LD-2    | 1.5       | 0.8            | 4.5       | 1.2                  |
| 757-3-5-11 | 6.1    | 6.0            | 4.8       | 0.8                  |

The levan sucrase-defective strain, LD-2 was transformed with the plsmid pSAZE3S containing the exocellular invertase gene and its secretion-accelerating gene of *Zymomonas mobilis* strain discosed in the Japanese Patent Application Hei 7 (1995)-252021, or the plasmid pSARH containing the gene of *Bacillus subtilis* encoding a levan sucrase with its reduced activity for levan formation. The production of cellulose by these transfomants in the CSL-Suc medium (Table 5) is shown in Table 25. The introduction of the above genes into the levan sucrase-defective strain has remarkably reduced the amount of levan as by-product in the production of cellulose from sucrose.

TABLE 25

Production of cellulose by the transformed LD-2

| Plasmid    | Cellulose (g/L) | Yield (%) | Polysaccharide (g/L) |
| ---------- | --------------- | --------- | -------------------- |
| none       | 1.5             | —         | 1.6                  |
| pSAZE3S    | 5.4             | 18.2      | 2.3                  |
| pSARH      | 5.2             | 19.0      | 4.6                  |
| 757-3-5-11 | 5.9             | 14.3      | 12.7                 |

EXAMPLE 9

Generation of Phlorizin-Resistant Strains

The strains showing resistance against the saccharide analog, phlorizin, were obtained from the mutants generated by the NTG treatment of the parent strain d-40-3 as in Example 3 (Table 26), and their BC productivity was evaluated (Table 27).

The strain d-40-3 and its NTG-treated mutants were inoculated on a plate containing the minimum medium with Glc (2%) at a concentration of 3,000 cells per plate and 4,000 cells per plate, respectively, and cultured for about one week at 28° C.

TABLE 26

Colony formation

|                          | Phlorizin |      |
| ------------------------ | --------- | ---- |
| Strains                  | 2 mM      | 5 mM |
| d-40-3                   | many      | none |
| Mutant treated with NTG  | many      | many |

One hundred strains were selected at random from the colonies of the NTG-treated mutants, which were formed in the medium containing 5 mM phlorizin, and subjected to a flask culture. As a result, the following e-51, e-61 and e-87 strains were obtained, which show higher BC productivity than that of the parent strain d-40-3.

TABLE 27

| Strain | BC (g/L) | Yield (%) |
| ------ | -------- | --------- |
| e-51   | 9.2      | 23.0      |
| e-61   | 7.7      | 19.2      |
| e-87   | 7.7      | 19.3      |
| d-40-3 | 7.6      | 19.0      |

After the completion of the culture, the solid contents in the flask were collected, washed with water to remove the medium components, and treated with 1% NaOH aqueous solution for 20 min. at 80° C. to remove the bacterial cells. The resulting cellulose was washed until the washing water became approximately neutral, and dried under vacuum for 12 hours at 80° C. to weigh the dry cellulose.

Calculation of Yield (%) against the consumed sugars $$Y_{BC}=BC/(RC_{MF}-RC_{BF})*100$$

YBC: Yield (%) against the consumed sugars
BC: Accumulated amount of BC (g/l)
RCMF: Sugar Concentration of the medium (g/l)
RCBF: Sugar Concentration of the medium after the culture (g/l)

Industrial Applicability

A larger amount of bacterial cellulose may be produced by culturing *Acetobacter xylinum* subsp. *nonacetoxidans,* the present resistant strains and the levan sucrase-defective strains, which have been derived and bred from the cellulose-producing bacteria, than by culturing the BPR 2001 strain in the medium containing especially sucrose or glucose as carbon sources.

We claim:

1. A biologically pure culture of *Acetobacter xylinum* subsp. *nonacetoxidans,* which is negative or very slightly positive in oxidation of acetates and lactates.

2. *Acetobacter xylinum* subsp. *nonacetoxidans* according to claim 1, which is FERM BP-5814.

3. *Acetobacter xylinum* subsp. *nonacetoxidans* according to claim 1, which is FERM BP-5815.

4. *Acetobacter xylinum* subsp. *nonacetoxidans* according to claim 1, which is FERM BP-5816.

5. A method for the production of a cellulosic product, which comprises culturing the cellulose-producing bacteria according to claim 1.

6. The method of claim 5, wherein the bacteria is FERM BP-5814.

7. The method of claim 5, wherein the cellulose-producing bacteria is FERM BP-5815.

8. The method of claim 5, wherein the cellulose-producing bacteria is FERM BP-5816.

* * * * *